United States Patent [19]

Eastman

[11] 4,389,337
[45] Jun. 21, 1983

[54] PROMOTED ZINC TITANATE CATALYST FOR THE DEHYDROGENATION OF ORGANIC COMPOUNDS

[75] Inventor: Alan D. Eastman, Bartlesville, Okla.

[73] Assignee: Phillips Petroleum Company, Bartlesville, Okla.

[21] Appl. No.: 340,401

[22] Filed: Jan. 18, 1982

Related U.S. Application Data

[62] Division of Ser. No. 125,436, Feb. 28, 1980, Pat. No. 4,327,238.

[51] Int. Cl.³ .................. B01J 21/06; B01J 23/06; B01J 23/10; B01J 23/18
[52] U.S. Cl. .................................. 252/462; 252/468; 252/475
[58] Field of Search .................. 252/462, 468, 475

[56] References Cited

U.S. PATENT DOCUMENTS

| | | | |
|---|---|---|---|
| 2,279,198 | 4/1942 | Huppke | 208/134 |
| 4,144,277 | 3/1979 | Walker et al. | 252/461 X |
| 4,304,687 | 12/1981 | Box et al. | 252/475 X |
| 4,313,017 | 1/1982 | McGinnis et al. | 252/475 X |
| 4,333,855 | 6/1982 | Gardner et al. | 252/475 X |

Primary Examiner—W. J. Shine

[57] ABSTRACT

The catalytic dehydrogenation of at least one dehydrogenatable organic compound which has at least one

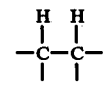

grouping is carried out in the presence of a zinc titanate catalyst. The selectivity of the zinc titanate catalyst is improved by at least one promoter selected from the group consisting of chromium oxide, antimony oxide, bismuth oxide, oxides of the lanthanides, oxides of the actinides, oxides thereof, and compounds convertible to the oxides thereof.

10 Claims, No Drawings

PROMOTED ZINC TITANATE CATALYST FOR THE DEHYDROGENATION OF ORGANIC COMPOUNDS

This application is a division of application Ser. No. 125,436, filed Feb. 28, 1980, now U.S. Pat. No. 4,327,238.

This invention relates to an improved catalytic process for the dehydrogenation of organic compounds, and a catalyst therefor.

Dehydrogenation processes for the conversion of organic compounds to compounds having a higher degree of unsaturation are well known. It is known that zinc titanate is useful as a dehydrogenation catalyst in the dehydrogenation of organic compounds. However, improving the selectivity of the zinc titanate catalyst is desirable. It is therefore an object of this invention to increase the selectivity of a zinc titanate catalyst and thus provide an improved process for the dehydrogenation of organic compounds.

In accordance with the present invention, at least one promoter selected from the group consisting of chromium, antimony, bismuth, the lanthanides, the actinides, oxides thereof and compounds convertible to the oxides thereof is utilized as a promoter for a zinc titanate catalyst in the dehydrogenation of organic compounds. The catalyst can be formed by combining zinc oxide and titanium dioxide by any of the methods known in the art to form zinc titanate. The promoter is then added to the zinc titanate. Once the catalyst has been prepared, organic compounds are dehydrogenated in the presence of the catalyst to produce organic compounds having a higher degree of unsaturation.

The dehydrogenation process is preferably carried out in cycles consisting of a reaction period and a regeneration period for the catalyst. The reaction period comprises contacting a dehydrogenatable organic compound with the dehydrogenation catalyst under suitable dehydrogenation conditions in the substantial absence of free oxygen to convert the dehydrogenatable organic compounds to compounds having a higher degree of unsaturation. After the reaction period, a free oxygen containing gas is passed in contact with the catalyst to regenerate the catalyst by burning off carbonaceous materials which may have formed on the catalyst.

The use of a promoter for the zinc titanate catalyst results in a higher selectivity for the catalyst. This results in a greater production of the desired product and a more economical operation of the dehydrogenation process.

Other objects and advantages of the invention will be apparent from the foregoing brief description of the invention and the appended claims as well as from the detailed description of the invention which follows.

The organic feedstocks which can be dehydrogenated in accordance with the present invention are dehydrogenatable organic compounds having from 2 to 12 carbon atoms per molecule and characterized by having at least one

grouping, i.e., adjacent carbon atoms, each having at least one hydrogen atom. Suitable compounds include paraffins, olefins, cycloaliphatics and alkyl aromatic compounds having from 2 to 12 carbon atoms per molecule. Particularly suitable are paraffins having from 2 to 5 carbon atoms per molecule and monoolefins having from 4 to 5 carbon atoms per molecule, branched or unbranched. Some examples of suitable hydrocarbon feedstocks are ethane, propane, butane, isobutane, pentane, isopentane, hexane, 2-methylhexane, n-octane, n-dodecane, 1-butene, 2-butene, 2-methyl-butene-1, 2-methyl-butene-2, 2-hexene, 1-octene, 3-methylnonene-4, 1-dodecene, cyclohexane, and the like and mixtures of any two or more thereof. Particularly appropriate is the conversion of ethane to ethylene, propane to propylene, butanes to butenes and butadiene, butenes to butadiene, and isopentane to isoamylenes and isoprene.

The dehydrogenation catalyst employed in the process of the present invention is a composition comprising zinc, titanium, and a promoter. The promoter is at least one member selected from the group consisting of chromium, antimony, bismuth, the lanthanides, the actinides, oxides thereof, and compounds convertible to the oxides thereof. Sufficient oxygen is present in the catalyst composition to satisfy the valence requirements of the zinc, titanium and promoter. The lanthanides are elements 57–71 and the actinides are elements 89–103 as set forth in the Periodic Table of the Elements, *Perry's Chemical Engineers Handbook*, fifth edition, McGraw-Hill, 1973. The preferred lathanides are lanthanum, cerium, samarium, praseodymium, neodymium, and dysprosium. The preferred actinides are thorium and uranium. The zinc and titanium are generally present as zinc titanate in the catalyst composition.

The zinc titanate base of the catalyst composition may be prepared by intimately mixing suitable portions of zinc oxide and titanium dioxide, preferably in a liquid such as water, and calcining the mixture in the presence of free oxygen at a temperature in the range of about 650° C. to about 1050° C., preferably in the range of about 675° C. to about 975° C. A calcining temperature in the range of about 800° C. to about 850° C. is most preferred because the surface area of the catalyst is maximized in this temperature range thus producing a more active catalyst. The titanium dioxide used in preparing the zinc titanate preferably has extremely fine particle size to promote intimate mixing of the zinc oxide and titanium dioxide. This produces a rapid reaction of the zinc oxide and titanium dioxide which results in a more active catalyst. Preferably the titanium dioxide has an average particle size of less than 100 millimicrons and more preferably less than 30 millimicrons. Flame hydrolyzed titanium dioxide has extremely small particle size and is particularly preferred in preparing the catalyst. The atomic ratio of zinc to titanium can be any suitable ratio. The atomic ratio of zinc to titanium will generally lie in the range of about 1:1 to about 3:1 and will preferably lie in the range of about 1.7:1 to about 2.1:1 because the activity of the catalyst is greatest for atomic ratios of zinc to titanium in this range. The term "zinc titanate" is used regardless of the atomic ratio of zinc to titanium.

The zinc titanate base of the catalyst composition may also be prepared by coprecipitation from aqueous solutions of a zinc compound and a titanium compound. The aqueous solutions are mixed together and the hydroxides are precipitated by the addition of ammonium hydroxide. The precipitate is then washed, dried and calcined as described in the preceding paragraph. This method of preparation is less preferred than the mixing method because the zinc titanate prepared by the coprecipitation method is softer than the zinc titanate prepared by the mixing method.

The promoter, at least one member of which is selected from the group consisting of chromium, antimony, bismuth, the lanthanides, the actinides, oxides thereof and compounds convertible to the oxides thereof, is present on the catalyst in the oxide form. The promoter can be added to the zinc titanate as powdered oxide and dispersed by any method known in the art such as rolling, shaking or stirring. The preferred method of adding the promoter is by impregnating the preformed zinc titanate with a solution of a compound of the promoting element, or compounds containing the promoting elements to be mixed, that becomes converted to the oxide during subsequent preparation of the catalyst.

The concentration of the promoter expressed as an element or mixtures of elements, can be any suitable concentration. The concentration of the promoter expressed as an element, will generally be in the range of about 0.3 to about 15 weight percent based on the weight of the zinc titanate prior to treatment with the promoter and will preferably be in the range of about 1 to about 5 weight percent based on the weight of the zinc titanate. The concentration of the promoter is preferably maintained low enough that the promoter acts as a promoter and not as a catalyst. This is especially important in the case of uranium which is a very active oxidation catalyst. The promoting elements are preferably used singularly and not in combinations except for combinations of the lanthanides and combinations of the actinides. Except for antimony, which apparently does not form nitrate compounds, the nitrates can conveniently provide a suitable form of the promoter with which to impregnate the zinc titanate. The salts of organic acids such as acetates, butyrates, or benzoates also can conveniently provide a suitable form of the promoter with which to impregnate the zinc titanate. Other suitable compounds of antimony are antimony tartrate, potassium antimonyl tartrate, and the like and mixtures of any two or more thereof. Following impregnation with a solution of the promoting element or elements, solvent is removed by warming, and the dried product is then calcined in a free oxygen-containing environment at about 800° C. to convert the element to its oxide. After this treatment, the catalyst is ready for use in the dehydrogenation process.

The dehydrogenation process of this invention can be carried out by means of any apparatus whereby there is achieved an alternate contact of the catalyst with the dehydrogenatable organic compound and thereafter of the catalyst with the oxygen-containing gaseous phase, the process being in no way limited to the use of particular apparatus. The process of this invention can be carried out using a fixed catalyst bed, fluidized catalyst bed or moving catalyst bed. Presently preferred is a fixed catalyst bed.

In order to avoid any casual mixing of the organic compound and oxygen, provision is preferably made for terminating the flow of feed to the reactor and subsequently injecting an inert purging fluid such as nitrogen, carbon dioxide or steam. Any suitable purge time can be utilized. The purge duration will generally range from about 1 minute to about 10 minutes and will more preferably range from about 3 minutes to about 6 minutes. Any suitable flow rate of the purge fluid may be utilized. Presently preferred is a purge fluid flow rate in the range of about 800 GHSV to about 1200 GHSV.

Any suitable dehydrogenation reaction time may be used in the dehydrogenation process. The dehydrogenation reaction time will generally be in the range of about 0.05 seconds to about 10 minutes and will preferably be in the range of about 0.1 second to about 5 minutes.

Any suitable time for the regeneration of the dehydrogenation catalyst can be utilized. The time for the regeneration of the dehydrogenation catalyst will generally range from about 1 to about 10 times the reaction period.

Any suitable catalytic dehydrogenation temperature can be employed which provides the desired degree of catalytic activity in the dehydrogenation of the organic feedstock. The dehydrogenation temperature will generally be in the range of about 426° C. to about 705° C. and will more preferably be in the range of about 538° C. to about 677° C.

The catalytic dehydrogenation process can be carried out at any suitable pressure. The pressure of the dehydrogenation reaction will generally range from about 0.05 to about 250 psia.

Any suitable feed rate for the organic feedstock can be utilized. The organic feedstock feed rate will generally be in the range of about 50 to about 5,000 volumes of gaseous feedstock per volume of catalyst per hour and will preferably be in the range of about 100 to about 2500 volumes of gaseous feedstock per volume of catalyst per hour.

The presence of steam is frequently beneficial to the dehydrogenation reaction. Generally, the steam-to-hydrocarbon molar ratio will range up to about 50:1. The steam-to-hydrocarbon molar ratio will preferably range from about 0.1:1 to about 20:1. An inert gaseous diluent, such as hydrogen or carbon dioxide, can also be utilized. If the inert gaseous diluent is utilized the amount used will generally be in the same amount as specified for the steam.

Steam can also be employed in admixture with the free oxygen-containing fluid during the regeneration period. The amount of free oxygen, from any source, supplied during the regeneration step will be in an amount sufficient to remove substantially all carbonaceous materials from the catalyst. The regeneration step is conducted at the same temperature and pressure recited for the dehydrogenation step although somewhat higher temperatures can be used, if desired.

The operating cycle for the dehydrogenation and regeneration process will generally include the successive steps of:

(1) contacting a dehydrogenation organic compound with the dehydrogenation catalyst;

(2) terminating the flow of the dehydrogenation organic compound;

(3) optionally, purging the catalyst with an inert fluid;

(4) contacting the dehydrogenation catalyst with free oxygen;

(5) terminating the flow of the free oxygen; and (6) optionally, purging the catalyst with an inert fluid before repeating step (1).

The following example is presented in further illustration of the invention.

EXAMPLE

Zinc titanate having the atomic ratio Zn:Ti=1.80 was prepared by combining 80.0 g of Degussa P-25 titanium dioxide and 146.7 g of Mallinckrodt zinc oxide in about 1000 ml of water and mixing for 10 minutes in a blender. The resulting slurry was dried in an oven at 130° C. to remove water and then calcined in air for three hours at 825° C. After cooling, the resulting zinc titanate was crushed and screened and a −16+40 mesh fraction obtained for testing and for treatment with various promoters.

Starting with the thus prepared zinc titanate, the catalysts tabulated in Table I were prepared by impregnating a weighed portion of zinc titanate with an aqueous solution containing a predetermined weight of the promoting element, as its nitrate. The resulting promoted zinc titanate was dried in an oven at 125° C. and finally calcining in air at 816° C. for 3 hours to convert the promoter to the oxide form. Concentrations cited represent the quantity of promoting element added to the zinc titanate, i.e. 10 wt. % M means the addition of one g of element M to 10 g of zinc titanate—not its concentration in the finished catalyst.

TABLE I

| Catalyst | Wt. % Promoter | Source of Promoter |
|---|---|---|
| 1 | 5 Cr | $Cr(NO_3)_3 \cdot 9 H_2O$ |
| 2 | 5 Mn | $Mn(NO_3)_2$ |
| 3 | 5 Fe | $Fe(NO_3)_3 \cdot 9 H_2O$ |
| 4 | 5 Co | $Co(NO_3)_2 \cdot 6 H_2O$ |
| 5 | 5 Ni | $Ni(NO_3)_2 \cdot 6 H_2O$ |
| 6 | 5 Ag | $AgNO_3$ |
| 7 | 5 La | $La(NO_3)_3 \cdot 5 H_2O$ |
| 8 | 5 Ce | $Ce(NO_3)_3 \cdot 6 H_2O$ |
| 9 | 5 Pr | $Pr(NO_3)_3 \cdot 5 H_2O$ |
| 10 | 5 Nd | $Nd(NO_3)_3 \cdot 6 H_2O$ |
| 11 | 5 Dy | $Dy(NO_3)_3 \cdot 5 H_2O$ |
| 12 | 5 Th | $Th(NO_3)_4 \cdot 4 H_2O$ |
| 13 | 5 U | $UO_2(NO_3)_2 \cdot 6 H_2O$ |
| 14 | 2.5 Cr + 2.5 U | See catalysts 1 and 13 above |
| 15 | 3 Sn | $SnSO_4$* |
| 16 | 3 Sb | $K(SbO)C_4H_4O_6 \cdot \frac{1}{2} H_2O$ |
| 17 | 3 Bi | $Bi(NO_3)_3 \cdot 5 H_2O$ |
| 18 | 0.6 Co | See catalyst 4 above |
| 19 | 0.7 Ni | See catalyst 5 above |
| 20 | 0.8 Cu | $Cu(NO_3)_2 \cdot 3 H_2O$ |
| 21 | 0.9 Ce | See catalyst 8 above |
| 22 | 1.2 Sm | $Sm(NO_3)_3 \cdot 6 H_2O$ |
| 23 | 1.5 U | See catalyst 13 above |
| 24 | — (control) | |

*After impregnation, tin was precipitated with $NH_4OH$ before drying and calcining.

Catalysts listed in Table I were used to dehydrogenate ethane to ethylene and hydrogen. All runs were made at atmospheric pressure and 666° C. At these conditions, thermodynamic equilibrium for the reaction is about 40 percent ethane conversion. The procedure for all runs was as follows: two to four cc portions of catalyst was placed in quartz reactors and the quartz reactors were installed in temperature-controlled furnaces. All fluids passed down-flow through the quartz reactors. After heating to 666° C. in air, catalysts were purged with nitrogen and then exposed to ethane during the process cycle. After purging with nitrogen, the catalysts were regenerated with air and the sequence was repeated. The gas hourly space velocity (GHSV) at STP was 500, 500, and 2000 for ethane, nitrogen, and air, respectively. One cycle consisted of 3 minutes nitrogen, 3 minutes ethane, 3 minutes nitrogen, and 6 minutes air. Generally, samples for analysis were taken after the catalyst had been subjected to at least 24 cycles. Analytical samples were prepared by accumulating the hydrocarbon product from twelve consecutive 3-minute intervals, then analyzing them in duplicate by gas liquid chromatography. The results shown in Table II are the average of duplicate analyses. Results from control catalyst 24 provide the basis against which runs with the promoted catalysts are to be compared. Catalysts 1–14 all were treated with 5 wt. % promoting element.

TABLE II

| Catalyst | Wt. % Promoter | Ethane Converted, % | Ethylene Yield, % | Selectivity, % |
|---|---|---|---|---|
| 1 | 5 Cr | 36 | 33 | 90 |
| 2 | 5 Mn | 32 | 25 | 80 |
| 3 | 5 Fe | 37 | 28 | 75 |
| 4 | 5 Co | 64 | 4 | 6 |
| 5 | 5 Ni | 82 | 0 | 0 |
| 6 | 5 Ag | 3 | 3 | 100 |
| 7 | 5 La | 32 | 30 | 94 |
| 8 | 5 Ce | 26 | 25 | 97 |
| 9 | Pr | 22 | 21 | 98 |
| 10 | 5 Nd | 24 | 23 | 98 |
| 11 | 5 Dy | 31 | 29 | 94 |
| 12 | 5 Th | 35 | 33 | 93 |
| 13 | 5 U | 36 | 30 | 82 |
| 14 | 2.5 Cr + 2.5 U | 4 | 3 | 89 |
| 15 | 3 Sn | 6 | 6 | 99 |
| 16 | 3 Sb | 36 | 32 | 89 |
| 17 | 3 Bi | 32 | 29 | 90 |
| 18 | 0.6 Co | 33 | 29 | 85 |
| 19 | 0.7 Ni | 30 | 23 | 78 |
| 20 | 0.8 Cu | 37 | 31 | 84 |
| 21 | 0.9 Ce | 37 | 33 | 90 |
| 22 | 1.2 Sm | 34 | 32 | 93 |
| 23 | 1.5 U | 32 | 30 | 93 |
| 24 | 0 | 37 | 31 | 83 |

Catalysts 3–5, promoted with group VIII elements, are all inferior to the control. Cobalt and nickel, while effecting very high conversion, showed essentially no selectivity to produce ethylene. Catalyst 6 showed that silver destroys most of the dehydrogenation activity. The presence of manganese on catalyst 2 was essentially without effect on the zinc titanate. Catalysts 1 and 7–12 (of the group treated with 5 wt. % promoter) increased selectivity for the zinc titanate. Catalyst 13 with 5 wt. % uranium had no significant effect on the zinc titanate, but catalyst 23, with only 1.5 wt. % uranium, increased significantly the selectivity to ethylene. The low weight percent of uranium is thought to be desired because of the high activity of uranium as an oxidizing catalyst. Surprisingly, catalyst 14, which contained equal concentrations of chromium and uranium was nearly inactive whereas catalysts containing these promoters separately are superior to the control. Catalysts 15–17, treated with 3 weight percent promoter, all showed good selectivity for ethylene but only catalysts 16 and 17 showed sufficient conversion of ethane to ethylene. Catalysts 18–23 were prepared to contain promoter equal in concentration to a monolayer on the zinc titanate base. This quantity of cobalt, nickel, and copper, in catalysts 18, 19, and 20, respectively, had no significant effect on the catalysts activity. However, catalysts 21–23 containing equivalent concentrations of cerium, samarium, and uranium, respectively, all showed selectivity superior to that of the control. Thus, in addition to chromium, antimony, and bismuth, the lanthanide and actinide elements improve the dehydrogenation activity of catalytic zinc titanate provided, apparently, that the concentration of the promoter is not large enough to allow the promoter to act as an oxidizing catalyst rather than a promoter.

Reasonable variations and modifications are possible within the scope of the disclosure and the appended claims to the invention.

That which is claimed is:

1. A catalyst composition comprising zinc, titanium and at least one promoter selected from the group consisting of antimony, bismuth, the lanthanides, the actinides, oxides thereof, and compounds convertible to the oxides thereof, wherein the concentration by weight of said at least one promoter in said catalyst composition is less than the total concentration by weight of said zinc and said titanium in said catalyst composition, wherein said zinc and titanium are present in said catalyst composition in the form of zinc titanate which is prepared by calcining a mixture of zinc oxide and titanium dioxide in the presence of free oxygen at a temperature in the range of about 650° C. to about 1050° C. and wherein said catalyst composition does not contain a metal selected from the group consisting of Group IB of the Periodic Table and Group VIIB of the Periodic Table.

2. A catalyst composition in accordance with claim 1 wherein said catalyst composition is a calcined catalyst composition and sufficient oxygen is present in said catalyst composition to satisfy the valence requirements of said zinc, said titanium and said at least one promoter.

3. A catalyst composition in accordance with claim 1 wherein the atomic ratio of zinc to titanium in said catalyst composition is in the range of about 1:1 to about 3:1.

4. A catalyst composition in accordance with claim 1 wherein the atomic ratio of zinc to titanium in said catalyst composition is in the range of about 1.7:1 to about 2.1:1.

5. A catalyst composition in accordance with claim 1 wherein the concentration of said at least one promoter expressed as an element or mixture of elements, is in the range of about 0.3 to about 15 weight percent based on the weight of said zinc titanate.

6. A catalyst composition in accordance with claim 1 wherein the concentration of said at least one promoter expressed as an element or mixture of elements, is in the range of about 1 to about 5 weight percent based on the weight of said zinc titanate.

7. A catalyst composition in accordance with claim 1 wherein said promoter is antimony, an oxide of antimony or a compound of antimony convertible to an oxide of antimony.

8. A catalyst composition in accordance with claim 1 wherein said promoter is bismuth, an oxide of bismuth or a compound of bismuth convertible to an oxide of bismuth.

9. A catalyst composition in accordance with claim 1 wherein said promoter is a lanthanide, an oxide of a lanthanide or a compound of a lanthanide convertible to an oxide of the lanthanide.

10. A catalyst composition in accordance with claim 1 wherein said promoter is an actinide, an oxide of an actinide or a compound of an actinide convertible to an oxide of the actinide.

* * * * *